US00PP11712P

United States Patent [19]

Lemon

[11] Patent Number: Plant 11,712

[45] Date of Patent: Dec. 19, 2000

[54] REGAL PELARGONIUM PLANT NAMED 'MAIDEN PETTICOAT'

[75] Inventor: David Lemon, Lompoc, Calif.

[73] Assignee: John Bodger and Sons Company, South El Monte, Calif.

[21] Appl. No.: 09/149,895

[22] Filed: Sep. 8, 1998

[51] Int. Cl.[7] ..... A01H 5/00

[52] U.S. Cl. ..... Plt./331

[58] Field of Search ..... Plt./331

[56] References Cited

U.S. PATENT DOCUMENTS

P.P. 8,909 9/1994 Walters ..... Plt./331

*Primary Examiner*—Bruce R. Campell
*Assistant Examiner*—Wendy A Baker
*Attorney, Agent, or Firm*—Fulwider Patton Lee & Utecht, LLP

[57] ABSTRACT

The claimed cultivar brings a new color to the Regal Maiden series of geraniums and is characterized by a white flower delicately streaked with purple shades over a medium green foliage. As with all Regal Maiden flowers, this cultivar exhibits superior rooting with a quick finishing time, compact plant habit and flowers early and easily.

1 Drawing Sheet

BACKGROUND OF THE NEW PLANT

The present invention comprises a new and distinct cultivar of *Pelargonium×domesticum* known by the varietal name 'Maiden Petticoat' (Oglevee No. 837, Bodger No. 3 PD15-6). The new variety was discovered in a selective breeding program by David Lemon at Bodger Seeds, Ltd., Lompoc, Calif. The new variety is a selection from the crossing of Bodger No. 2PD23-3 (unpatented) which produces a lavender flower, with Bodger No. 10PD11-4 (unpatented) which is a white flower characterized by a purple blotch.

The new cultivar was first asexually reproduced by cuttings at Oglevee Ltd., located at 152 Oglevee Lane, Connellsville, Pa., 15425 and has been repeatedly asexually reproduced by cuttings at Oglevee Ltd. in Connellsville, Pa. It has been found to retain its distinctive characteristics through successive propagations.

The new cultivar, was grown in a glass greenhouse in Connellsville, Pa., using full light, 60° Fahenheit night temperature, 68° Fahrenheit day temperature, and grown in a soilless media using a constant fertilizer of 200–250 parts per million of Nitrogen and Potassium, in full light. The claimed plant was grown from a rooted cutting, potted in a 10 cm pot and exhibited a eight week response time from the rooted cutting to a flowering plant.

Bloom height is 5.0 to 10.0 cm above foliage. Observed number of florets is 10 to 18 per umbel.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted in a 20 cm pot on approximately Jan. 17, 1998 and flowering on approximately Mar. 14, 1998, under full light in the greenhouse, and color readings were taken in the Oglevee office under 200–220 foot candles of cool white fluorescent light using The Royal Horticultural Society of London Colour Chart.

THE PLANT

Classification:
- *Botanical.*—*Pelargonium×domesticum.*
- *Commercial.*—Regal Geranium 'Maiden Petticoat'.

Form: Upright mound habit.
- *Height.*—20–22 cm above the top of pot.
- *Growth.*—Compact mound habit.
- *Strength.*—Needs no artificial support; Quick rooting.

Foliage: Slightly shiny; Medium green; Stalked leaf attachment.

Leaves:
- *Size.*—8–9 cm across when fully expanded.
- *Shape.*—Depressed ovate; truncate base.
- *Margin.*—Serrately lobed.
- *Texture.*—Pubescent; leathery.
- *Color.*—Top: Green Group 137B. Bottom: Green Group 137C. Zone: None present.
- *Ribs and veins.*—Palmate venation. Color: Yellow-Green Group 146C.

Petioles:
- *Length.*—3.5–5.0 cm.
- *Color.*—Yellow-Green Group 146C.

Stem:
- *Color.*—Yellow-Green Group 146C.
- *Internode length.*—3.0–4.5 cm.

THE BUD (UMBEL)

This information refers to bud size and shape subsequent to elongation but before florets have begun to open.

Shape: Elliptical cluster: This information describes the overall shape of the entire bud cluster or umbel. Individual bud shape is also elliptical or oval. Approximate number of buds per cluster is 15–20.

Size: 3.0–5.0 cm across; buds just showing some color.

INFLORESCENCE

Blooming habit: Continuous flowering.

Borne: Umbel; Florets on pedicel; Pedicel on peduncle.

Closed florets: Bud size: 2.0–2.5 cm; bud just beginning to show color.

Size: Fully open bloom: 5.5–6.5 cm across.
Open florets:
*Form.*—Slightly cupped; ruffled.
*Color.*—Top: Base is White Group 155D; Outer edge is Red Group 56D; Veining and streaking starts at base ranging from Red-Purple Group 71A to Red-Purple Group 71B; the blotch in the center is from Greyed Purple Group 187B. Bottom: White Group 155D with a Red-Purple Group 70C blotch and Red-Purple Group 61A streaks showing through. Eye: None.
*Petals.*—5 in number.
*Size.*—2.5–3.5 cm.
*Texture and appearance.*—Satiny, slightly shiny bloom whose appearance at a distance is a white flower streaked with shades of purple above medium green foliage.
Petaloids:
*Quantity.*—0 petaloids.
Pedicel:
*Length.*—2.0—3.0 cm.
*Color.*—Yellow-Green Group 144A.
Peduncle:
*Length.*—4.0–6.0 cm.
*Color.*—Yellow-Green Group 144A.
Persistence:
*Disease resistance.*—Not known.
*Lasting quality.*—Slow to shatter and continuous blooming.

REPRODUCTIVE ORGANS

Stamens:
*Anthers.*—Length: 3.0–4.0 mm.
*Filaments.*—Length: 9.0–11.0 mm. Color: White.
*Pollen.*—None.
Pistils:
*Number.*—1.
*Length.*—2.0 cm.
*Stigma.*—Color: Red-Purple Group 71A; 5 parted.
*Style.*—Length: 1.2 cm.
Ovaries:
*Color.*—Light Green; Pubescent.
*Length.*—4.0–5.0 mm.
Fruit: None.

GENERAL CHARACTERISTICS

'Maiden Petticoat' brings a new and distinct addition to the Regal Maiden Series which is a group of varieties having large blooms with a compact medium plant size making them suitable for growing in a 13 cm pot. Although not a clear white, 'Maiden Petticoat' presents a white flower delicately veined with shades of purple. 'Maiden Petticoat' exhibits quick rooting speed and early flowering.

I claim:

1. A new and distinct variety of Geranium plant, substantially as shown and described.

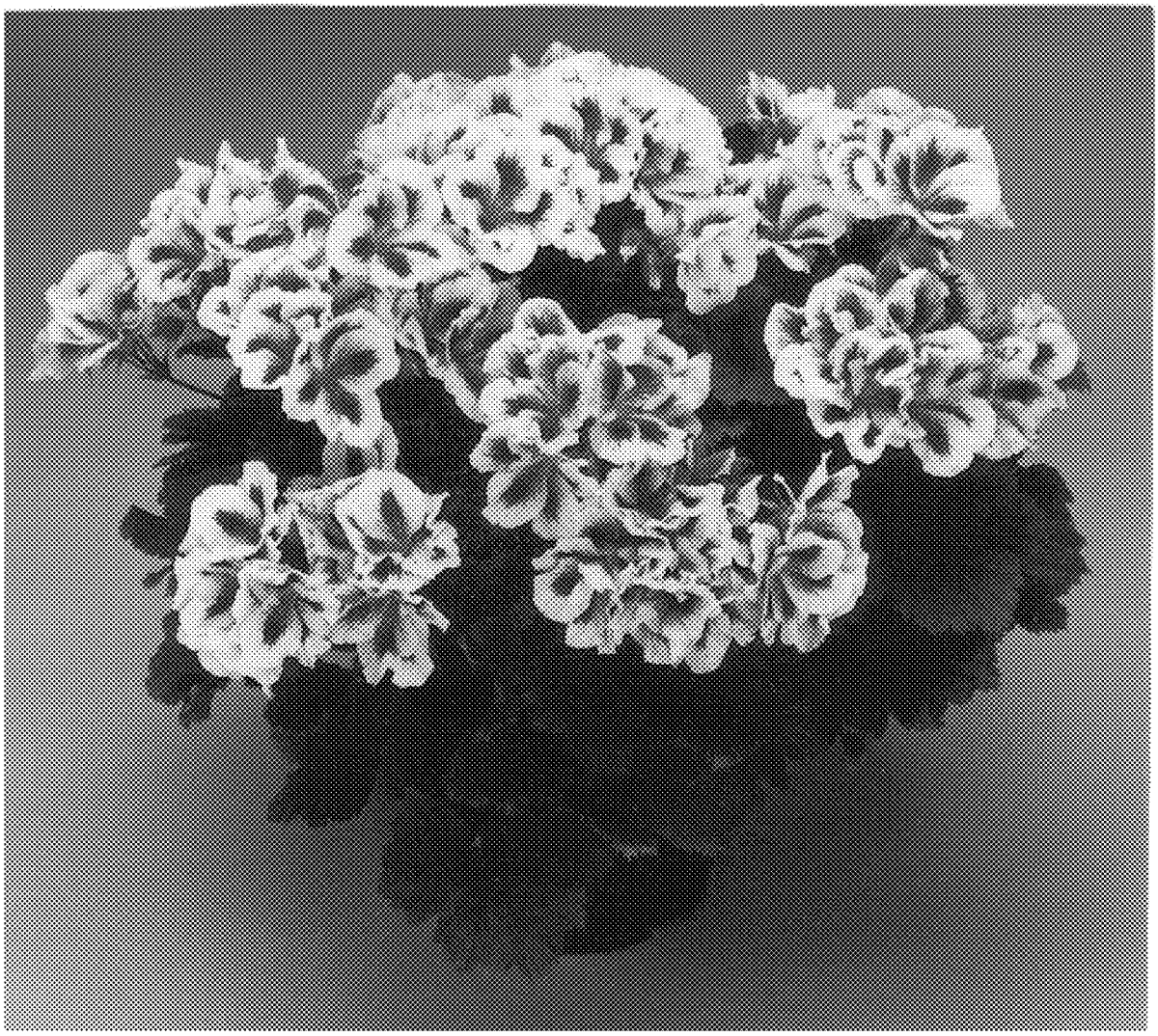

* * * * *